United States Patent [19]

Bélangér et al.

[11] 4,256,152

[45] Mar. 17, 1981

[54] APPARATUS FOR PREPARING AMPULLAS

[75] Inventors: Guy Bélangér; Gilles Missout, both of St. Bruno, Canada

[73] Assignee: Hydro-Quebec, Quebec, Canada

[21] Appl. No.: 54,795

[22] Filed: Jul. 5, 1979

Related U.S. Application Data

[62] Division of Ser. No. 963,518, Nov. 24, 1978.

[30] Foreign Application Priority Data

Sep. 18, 1978 [CA] Canada .................................. 311484

[51] Int. Cl.³ .............................................. B65B 3/04
[52] U.S. Cl. ...................................... 141/70; 141/83; 141/244
[58] Field of Search ...................................... 141/1–12, 141/37–70, 237–248, 83; 204/195 R, 1 T, 195 P; 364/497, 500; 324/29, 464; 422/81

[56] References Cited

FOREIGN PATENT DOCUMENTS 904690 3/1945 France ..................................... 141/244

*Primary Examiner*—Houston S. Bell, Jr.
*Attorney, Agent, or Firm*—Schwartz, Jeffery, Schwaab, Mack, Blumenthal & Koch

[57] ABSTRACT

The invention relates to an apparatus for measuring the concentration of gaseous hydrogen dissolved in a liquid substance. The apparatus comprises an electrochemical cell constituted of a polymeric membrane in contact with a sample of the liquid substance and which is permeable to hydrogen, of an electrolyte capable of causing an oxydation reaction of the hydrogen diffused through the polymeric membrane, at a first electrode, and a reduction reaction of an oxygenated gas at a second electrode, so as to deliver an electric current proportional to the hydrogen concentration to be measured. An electrovalve operates, when activated, to exhaust the liquid substance sample at a predetermined instant in the measuring process. Moreover, the circuit amplifies a voltage corresponding to the value of the current proportional to the concentration, which current flows through a load resistance mounted in parallel across the first and second electrodes and the input of the amplifying circuit. A display device is connected to the output of the amplifying circuit and supplies a digital measure of the hydrogen concentration in the liquid substance. A control unit determines the operation times of the electrochemical cell, of the electrovalve as well as of the digital display device pursuant to a predetermined sequence.

3 Claims, 1 Drawing Figure

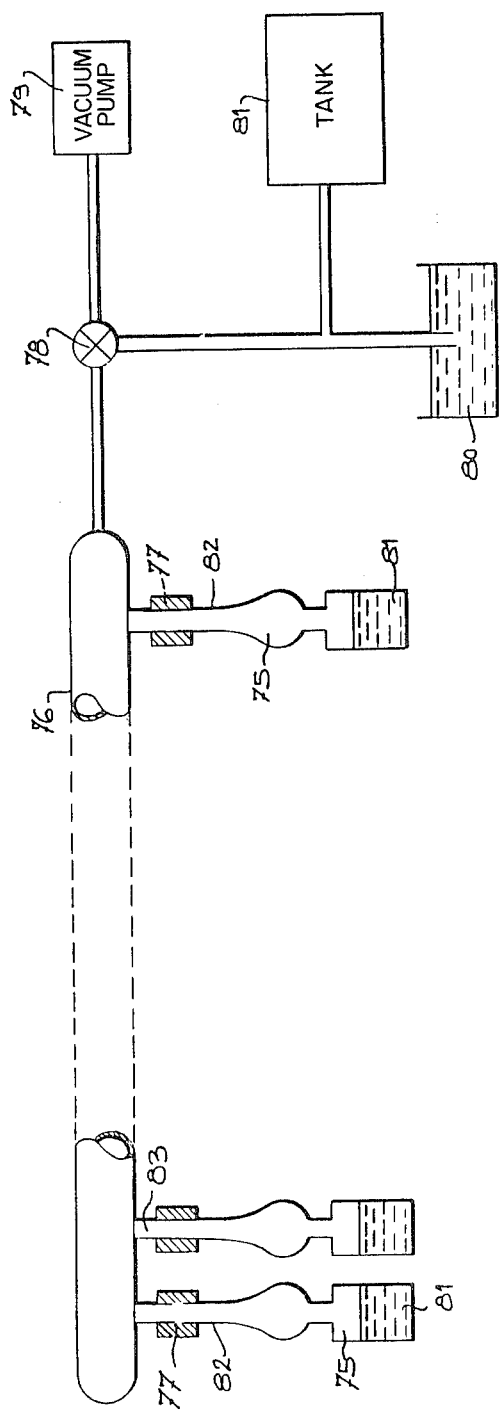

APPARATUS FOR PREPARING AMPULLAS

BACKGROUND OF THE INVENTION

The present application is a division of U.S. patent application Ser. No. 963,518 filed on Nov. 24, 1978.

The present invention relates to an apparatus for preparing ampullas useful in the calibration of an apparatus for detecting and measuring the concentration of hydrogen gas dissolved in a liquid substance.

More especially, the present invention relates to an apparatus for preparing ampullas useful for the calibration of a detecting apparatus such as that disclosed in U.S. patent application Ser. No. 963,581, which detecting apparatus works according to an automatic operation process and following a pre-established sequence.

The apparatus disclosed in U.S. patent application Ser. No. 963,518 comprises an electrochemical detection device including an electrochemical cell operative to determine the concentration of hydrogen gas in a sample of a liquid substance and to generate a current of a value proportional to that concentration; a device, connected to the detection device, for draining the liquid sample therefrom; a display device for displaying the concentration detected by the detection device; and a control circuit for controlling operation times of the detection device, the draining device and display device pursuant to a predetermined process sequence.

The sample of the liquid of which the hydrogen content is to be determined is usually taken by means of a syringe and injected through one opening in the electrochemical cell. The air then contained in the cell is exhausted exteriorly through another opening. After each measurement, the analyzed sample is drained either automatically, when a given number of time intervals of the operation sequence has elapsed, or manually by means of a button, a triggering relay and an electro valve 36. The used liquid is then stored in a tank provided with an hermetic cover to avoid any splashing thereof during transportation of the apparatus.

In order to obtain an accurate reading from the display device about the hydrogen content of the liquid under consideration, a calibration of the apparatus is necessitated from time to time. That calibration is effected through the use of a liquid identical to that of the sample, which liquid contains a known concentration in hydrogen gas. This calibration liquid can be either housed in a cylindrical tank firmly held in position inside the apparatus or stocked out of the apparatus in a plurality of individual constant volume gas amplullas.

SUMMARY OF THE INVENTION

It is the object of the present invention to provde an apparatus for preparing ampullas that can be used as such for the calibration of a detecting apparatus of the above mentioned type.

In accordance with the invention, this object is achieved with an apparatus for preparing ampullas useful in the calibration of an apparatus for detecting and measuring the hydrogen gas content in a liquid substance, said preparing apparatus comprising an elongated glass tube having a closed extremity and an open extremity, said glass tube being provided with a plurality of conduits disposed along its generatrix; a plurality of ampullas each having approximately half of its volume filled with a liquid identical to said liquid substance, said ampullas being hermetically connected to said tube conduits; a three-way valve secured to said open extremity of the tube and communicating either with a vacuum pump for degasifying the liquid contained in the ampullas, or with a reservoir containing a nitrogen-hydrogen mixture in a proportion of about 1 to 3% vol./vol. for saturating the liquid substance contained in each ampulla with a given quantity of gaseous hydrogen after having degasified said liquid substance; and means for sealing the ampullas after having saturated the liquid substance contained therein.

BRIEF DESCRIPTION OF THE DRAWING

A preferred embodiment of the invention will now be described with reference to the FIGURE which illustrates an apparatus according to the invention for preparing glass ampullas containing a calibration liquid.

DETAILED DESCRIPTION OF THE PREFERRED EMBODIMENTS

The apparatus shown on the FIGURE is useful for the preparation of individual constant volume glass ampullas for instance of a 10 cc capacity, for the calibration of the electrochemical cell of a detecting apparatus such as that disclosed in U.S. patent application Ser. No. 963,518, each ampulla containing about 5 cc of calibration liquid. The apparatus illustrated in this FIGURE and its operation mode permit the preparation of a few dozen ampullas at once. The system is generally constituted of an elongated glass tube 76 provided with a series of conduits 83 disposed along the longitudinal wall of the tube, each conduit communicating with one ampulla 75. One extremity of the glass tube 76 is connected to a three-way valve 78 which is in turn connected to a vacuum pump 79 and to a tank 81 containing a nitrogen-hydrogen mixture in a proportion of about 1 to 3% vol./vol. The conduit connecting valve 78 to tank 81 also leads to a reservoir 80 containing water and acting as a pressure indicator. Besides, rubber bands 77 sealingly connect ampullas 81 to conduits 83 and tube 76.

Once the ampullas have been connected to conduits 83, the degasifying of the liquid 81 in each ampulla is effected by activating the vacuum pump 79 for about a few hours. Then, the conduits connecting valve 78 to tank 81 are cleared out through a bubbling of the gaseous mixture for a few minutes, and thereafter, valve 78 is manipulated so as to fill tube 76 and ampullas 75 with the gaseous mixture, the latter step being performed under atmospheric pressure. Finally, the ampullas are successfully sealed at their neck area 82 and stored for a few weeks. After that storing period, one or more ampullas from the same batch are analyzed in order to determine their hydrogen content. For that purpose, the ampulla is scrated with a file at the nect level and then broken through a lateral pressure with the thumb. The hydrogen gas concentration thus determined is indicated on the other ampullas preapred under the same conditions. That calibration method has provided excellent results in terms of accuracy and stability in the calibration procedure and consequently may be widely used, particularly when a more compact and light weight measuring apparatus is desired.

We claim:

1. An apparatus for preparing ampullas useful in the calibration of a means for detecting and measuring the hydrogen gas content in a liquid substance, said apparatus comprising:

an elongated glass tube having a closed extremity and an open extremity, and provided with a plurality of conduits disposed along a generatrix of said tube;

a plurality of ampullas, each ampulla having approximately half of its volume filled with a liquid identical to said liquid substance and being hermetically connected to said tube conduits;

a vacuum pump means for degasifying the liquid contained in the ampullas;

a reservoir containing a nitrogen-hydrogen mixture in a proportion of about 1 to 3% vol./vol. for saturating, in the liquid in each ampulla, a given quantity of gaseous hydrogen; and a three way valve means, secured to said open extremity of the tube, for selectively placing said tube in communication with either said pump means or said reservoir.

2. A apparatus as claimed in claim 1, wherein a rubber band sealingly joins each ampulla to each conduit of said tube.

3. A apparatus as claimed in claim 1, wherein a pressure indicator is connected to said reservoir containing the nitrogen-hydrogen mixture.

* * * * *